US00PP29735P2

(12) United States Plant Patent
Klemm et al.

(10) Patent No.: US PP29,735 P2
(45) Date of Patent: Oct. 9, 2018

(54) ***DIANTHUS* PLANT NAMED 'KLEDP16186'**

(50) Latin Name: *Dianthus caryophyllus*
Varietal Denomination: KLEDP16186

(71) Applicant: Klemm+Sohn GmbH & Co. KG, Stuttgart (DE)

(72) Inventors: Nils Klemm, Stuttgart (DE); Lena Gutbrodt, Bempflingen (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 7 days.

(21) Appl. No.: 15/731,217

(22) Filed: May 4, 2017

(51) Int. Cl.
*A01H 5/02* (2018.01)

(52) U.S. Cl.
USPC ..... Plt./273

(58) Field of Classification Search
USPC ..... Plt./263.1, 273
See application file for complete search history.

*Primary Examiner* — Susan McCormick Ewoldt
*Assistant Examiner* — Karen M Redden
(74) *Attorney, Agent, or Firm* — Barbara Campbell; Bethany Reid Roahrig; Cochran Freund & Young LLC

(57) ABSTRACT

A new *Dianthus* plant particularly distinguished by dark-purple flowers with white margins, a strong fragrance, and an upright habit, is disclosed.

1 Drawing Sheet

Genus and species: *Dianthus caryophyllus.*
Variety denomination: 'KLEDP16186'.

CROSS-REFERENCE TO RELATED APPLICATIONS

A Community Plant Variety Rights application for the instant variety was filed on May 6, 2016, File No. 2016/1116. 'KLEDP16186' has not been sold or made publicly available more than one year prior to the filing of the instant application.

BACKGROUND OF THE NEW PLANT

The present invention comprises a new and distinct variety of *Dianthus*, botanically known as *Dianthus caryophyllus*, and hereinafter referred to by the variety name 'KLEDP16186'. 'KLEDP16186' originated from a branch mutation of the proprietary mutation parent 'KLEDP07088' (unpatented) in March 2010 in Stuttgart, Germany.

In August 2012, 'KLEDP16186' was first vegetatively propagated by vegetative cuttings. 'KLEDP16186' was found to reproduce true to type in successive generations of asexual propagation in Stuttgart, Germany via vegetative cuttings.

SUMMARY

The following are the most outstanding and distinguishing characteristics of this new variety when grown under normal horticultural practices in Stuttgart, Germany.

1. Dark-purple flowers with white margins;
2. A strong fragrance; and
3. An upright habit.

DESCRIPTION OF THE PHOTOGRAPH

This new *Dianthus* plant is illustrated by the accompanying photograph of a plant approximately 2 to 3-months old and grown in a greenhouse in Stuttgart, Germany. The photograph shows the whole plant, including the flowers and foliage and buds and was taken in April 2016 in Stuttgart, Germany.

The colors shown are as true as can be reasonably obtained by conventional photographic procedures.

DESCRIPTION OF THE NEW VARIETY

The following detailed descriptions set forth the distinctive characteristics of 'KLEDP16186'. The data which define these characteristics were collected from asexual reproductions carried out in Stuttgart, Germany. Data was collected in April 2017 on 7-month old plants grown in a plastic greenhouse. Color references are to The R.H.S. Colour Chart of The Royal Horticultural Society of London (R.H.S.), 5$^{th}$ edition (2007).

Classification:
- *Family.*—Caryophyllaceae.
- *Botanical.*—*Dianthus caryophyllus.*
- *Common.*—Pot carnation.
- *Designation.*—'KLEDP16186'.

Parentage:
- *Mutation parent.*—The proprietary *Dianthus* variety 'KLEDP07088' (unpatented).

Plant:
- *Plant form.*—Upright, potted plant.
- *Plant height.*—15.0 cm to 17.0 cm.
- *Plant diameter or spread.*—18.0 cm to 22.0 cm.
- *Propagation type.*—Vegetative cuttings, stem cutting.
- *Time to produce a rooted young plant.*—14 to 16 days.
- *Root description.*—White, fine.
- *Rooting habit (shape).*—Lanceolate.

Lateral branches:
- *Length.*—11.0 cm to 13.0 cm.
- *Diameter.*—0.3 cm to 0.5 cm.
- *Internode length.*—2.5 cm to 4.0 cm.
- *Number of internodes per branch/stem.*—4 to 6.
- *Node length.*—0.3 cm to 0.5 cm.

*Node diameter.*—0.4 cm.
*Texture.*—Smooth.
*Color.*—RHS 144.
*Branch/stem appearance.*—Solid.

Foliage:
*Arrangement.*—Opposite.
*Length.*—6.0 cm to 8.0 cm.
*Width.*—0.5 cm to 0.7 cm.
*Shape.*—Lanceolate.
*Apex.*—Acute.
*Base.*—Obtuse.
*Margin.*—Entire.
*Texture (both upper and lower surfaces).*—Smooth.
*Immature leaf color.*—Upper surface: RHS 143A. Lower surface: RHS 139B.
*Mature leaf color.*—Upper surface: RHS 139A. Lower surface: RHS N137A.
*Venation pattern.*—Palmate.
*Venation color.*—Upper surface: RHS 139A. Lower surface: RHS N137A.

Flowers:
*Flower type and habit.*—Round, double, small sprays.
*Fragrance.*—Present.
*Natural flowering season.*—Spring to fall.
*Position of flowers relative to the foliage.*—Slightly above.
*Number of flowers per spray.*—3 to 4.
*Flower longevity on the plant.*—10 to 14 days.
*Buds.*—Length: Approximately 2.0 cm. Diameter: 1.0 cm to 1.2 cm. Shape: Elliptic. Color: RHS 143A and 137A. Extrusion of the styles at the bud stage: Absent.
*Corolla.*—Quantity of petals and arrangement: 16 to 18. Corolla height: 1.5 cm to 2.0 cm. Petal length: 3.0 cm. Petal width: 1.5 cm to 2.0 cm. Petal shape: Spoon-shaped. Petal apex: Obtuse. Petal base: Acute. Petal margin: Crenate. Depth of petal margin: Medium. Petal texture (both upper and lower surfaces): Smooth. Petal color: Immature: Upper surface: RHS N79A and N155B. Lower surface: RHS 76C. Mature: Upper surface: RHS 77A and N177B. Lower surface: RHS 69D.
*Calyx.*—Quantity of sepals and arrangement: Composed of 5 sepals. Shape: Campanulate. Calyx height: 2.0 cm to 2.4 cm. Calyx diameter (at the apex): 0.8 cm to 1.0 cm. Sepal texture (both upper and lower surfaces): Smooth. Sepal color: Upper surface: RHS 137A. Lower surface: RHS 137D.

Peduncles:
*Length.*—10.0 cm to 14.0 cm (from bud to soil); Approximately 1.0 cm from bud to first nodium.
*Diameter.*—0.2 cm.
*Strength.*—Moderate.
*Texture.*—Smooth.
*Color.*—RHS 139A.

Reproductive organs:
*Stamens.*—Quantity per flower: Moderate. Filament length: 0.4 cm to 0.6 cm. Filament color: RHS 157B. Anther length: 0.1 cm. Anther diameter: 0.05 cm. Anther color: RHS 20 B. Pollen amount: Sparse.
*Pistils.*—Quantity per flower: 1. Pistil length: 0.1 cm. Style length: 1.6 cm to 1.8 cm. Style color: RHS 157C. Stigma shape: Filamentous. Stigma color: RHS N80A. Ovary size: 0.8 cm to 1.0 cm. Ovary shape: Oval. Ovary color: RHS N144 A and RHS 145A.

Fruit and seed set: Seed is sometimes observed, but no information on the seed is available.

Disease and pest/insect resistance: No disease and pest/insect resistance observed.

COMPARISON WITH PARENTAL LINE AND KNOWN VARIETY

'KLEDP16186' is distinguished from the mutation parent as described in Table 1.

TABLE 1

Comparison with Parental Line

| Characteristic | 'KLEDP16186' | Mutation Parent 'KLEDP07088' |
|---|---|---|
| Petal color | Dark purple with white margins | Light pink with purple stripes and center |

'KLEDP16186' can be compared to the commercial *Dianthus* variety 'Sunflor Bianca' (Patent status unknown). Differences between the varieties are described in Table 2.

TABLE 2

Comparison with Similar Variety

| Characteristic | 'KLEDP16186' | 'Sunflor Bianca' |
|---|---|---|
| Fragrance | Strong | Moderate to absent |
| Flower size | Large | Medium |

We claim:

1. A new and distinct variety of *Dianthus* plant designated 'KLEDP16186' as illustrated and described herein.

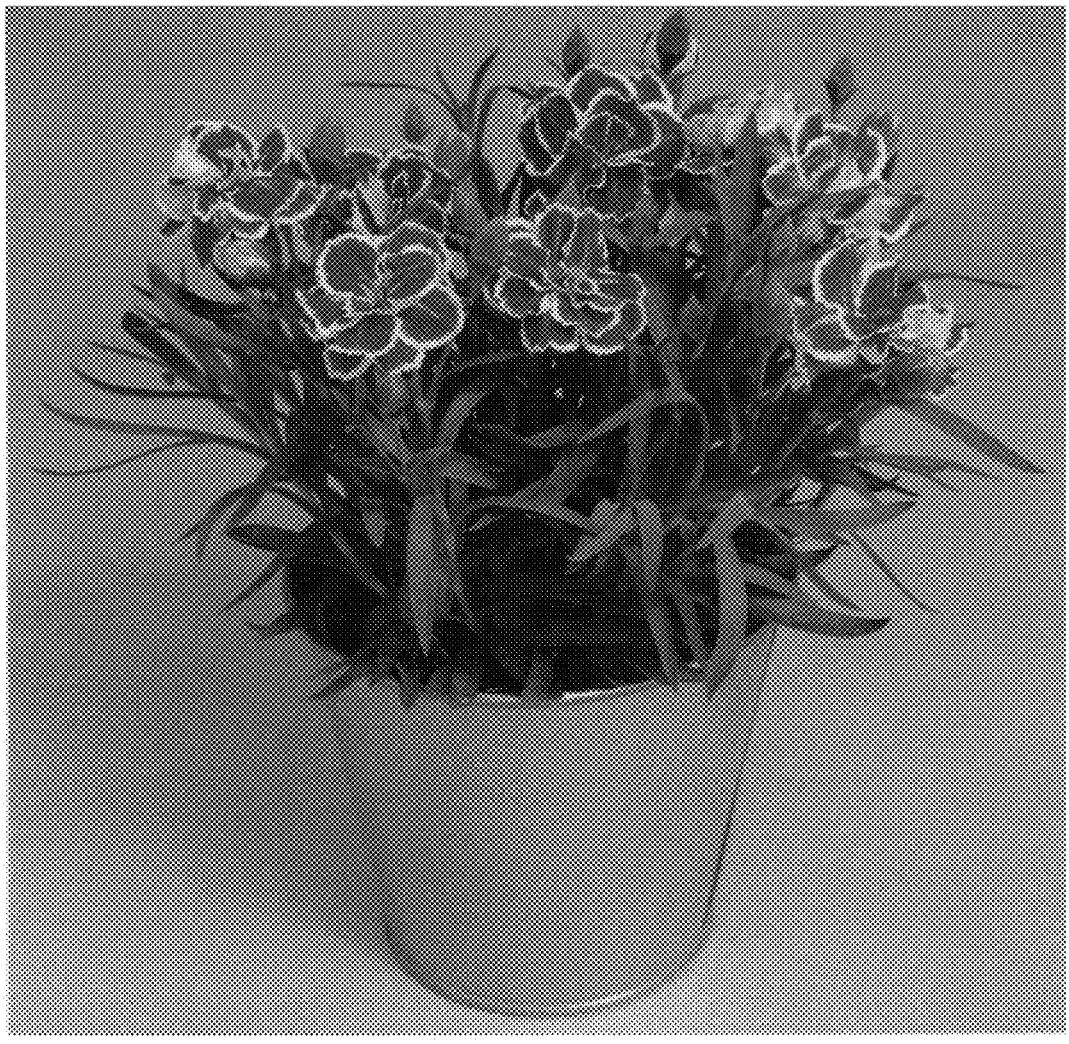

* * * * *